United States Patent
Cina et al.

(10) Patent No.: US 7,987,101 B2
(45) Date of Patent: Jul. 26, 2011

(54) ELECTRONIC BENEFICIARY SUCCESSOR PLANNING

(75) Inventors: Miroslav Cina, Hanhofen (DE); Erik Dworog, Heidelberg (DE)

(73) Assignee: SAP AG, Walldorf (DE)

( * ) Notice: Subject to any disclaimer, the term of this patent is extended or adjusted under 35 U.S.C. 154(b) by 1161 days.

(21) Appl. No.: 11/514,491

(22) Filed: Aug. 31, 2006

(65) Prior Publication Data
US 2008/0071556 A1 Mar. 20, 2008

(51) Int. Cl.
G06Q 10/00 (2006.01)
G06Q 50/00 (2006.01)
A61B 5/00 (2006.01)
G06F 19/00 (2006.01)

(52) U.S. Cl. .................................. 705/2; 705/3
(58) Field of Classification Search .................. 705/2–3
See application file for complete search history.

(56) References Cited

U.S. PATENT DOCUMENTS

| 5,913,198 A * | 6/1999 | Banks .................. 705/36 R |
| 6,411,939 B1 * | 6/2002 | Parsons .................... 705/35 |
| 2002/0156657 A1 * | 10/2002 | de Grosz et al. ............ 705/4 |
| 2004/0117202 A1 * | 6/2004 | Winklevoss et al. ......... 705/1 |

* cited by examiner

Primary Examiner — Luke Gilligan
Assistant Examiner — Joy Chng
(74) Attorney, Agent, or Firm — Kenyon & Kenyon LLP

(57) ABSTRACT

Beneficiary successor planning is performed by the examination of beneficiary data from a new benefits request and determining available succession benefit plans. The successor planning includes re-using existing beneficiary data associated with the request as well as determining the current requested benefits plan. From this information, the successor planning includes generating successor benefit plans which can re-use the beneficiary information that is available and may also indicate triggering events that, when these events occur, would render the successor plan in effect. Through this planning, manual data entry is reduced and the successor benefit plans are automatically generated.

14 Claims, 4 Drawing Sheets

ELECTRONIC BENEFICIARY SUCCESSOR PLANNING

COPYRIGHT

A portion of the disclosure of this patent document contains material that is subject to copyright protection. The copyright owner has no objection to the facsimile reproduction by anyone of the patent document or patent disclosure as it appears in the Patent and Trademark Office patent file or records, but otherwise reserves all copyright rights whatsoever.

BACKGROUND

The present invention relates generally to a benefits processing system and more specifically to the receipt of a benefits application and the generation of a benefits plan and a succession plan based on the benefits plans.

Existing social benefit plans include various levels of data management responsibilities. Social benefit plans may include government based plans, for example such as welfare, medical assistance or social security plans. Social benefit plans may also include non-government based benefits, such as company provided health care or other types of benefits.

In managing the various amounts of beneficiary information, these plans include back-end computing systems to actively inventory and track the benefit information. This information includes the name and addresses of the beneficiaries, as well as the information relating to the particular benefits received.

For example, the benefits software system may include a database of information for various benefits, such as military information for military benefits, age information for age-related benefits, family status for social welfare benefits, among others. These benefit systems and the software included thereon are single-dimensional providing information solely on existing benefit situations. These systems are also limited in the ability to share information across numerous systems.

In the existing systems, if a person or organization wishes to apply for a social benefit, this typically entails an enrollment process. This process includes the collection of various amounts of personal information. This information is then manually entered into the benefits system associated with the specific intended benefit. This manual entry is very time consuming, not only for the benefits coordinator running the software, but the person or organization, i.e. intended beneficiary, who must proceed through this process in order to receive the benefit.

Under existing systems, the user manually enters this information for the single benefit plan. The existing systems do not have the ability to access a database of user information to extract previously entered information because the vast difference in information required for different social benefits. For example, a beneficiary registering to receive a medical-based social benefit enters different information than a beneficiary registering to receive a job-assistance social benefit. Therefore, the existing systems do not overlap the beneficiary information.

Additionally, the existing systems address the present benefits plan without considering or addressing future benefit plans. It is recognized that as different factors change, the terms and conditions of the social benefit plan also change. For example, as a beneficiary ages, the benefits may also adjust. Therefore, it is important for the benefits software system to actively monitor the different conditions of the benefit plans.

As the conditions for benefits change, benefits themselves change. The existing systems do not provide an automated successor planning process. Rather, these systems require user-intervention, such as manually determining a successor plan and re-entering benefits information to generate the new social benefits application.

As these social benefits plan are typically government based operations, overhead associated with the processing of social benefits detracts from the funding or other resources available to beneficiaries. The existing systems require extensive amounts of manual data entry and do not include back end processing support to streamline the application process. This streamlined process is unavailable not only for new social benefit applications, but also for the continued processing of benefits for when the benefit conditions change.

DETAILED DESCRIPTION

Beneficiary successor planning is performed by the examination of beneficiary data from a new benefits request and determining available succession benefit plans. The successor planning includes re-using existing beneficiary data associated with the request as well as determining the current requested benefits plan. From this information, the successor planning includes generating successor benefit plans which can re-use the beneficiary information that is available and may also indicate triggering events that, when these events occur, would render the successor plan in effect, for example if a beneficiary reached a certain age and the type of benefit or the beneficiary would then change. Through this planning, manual data entry is reduced and the successor benefit plans are automatically generated.

Figure 1:
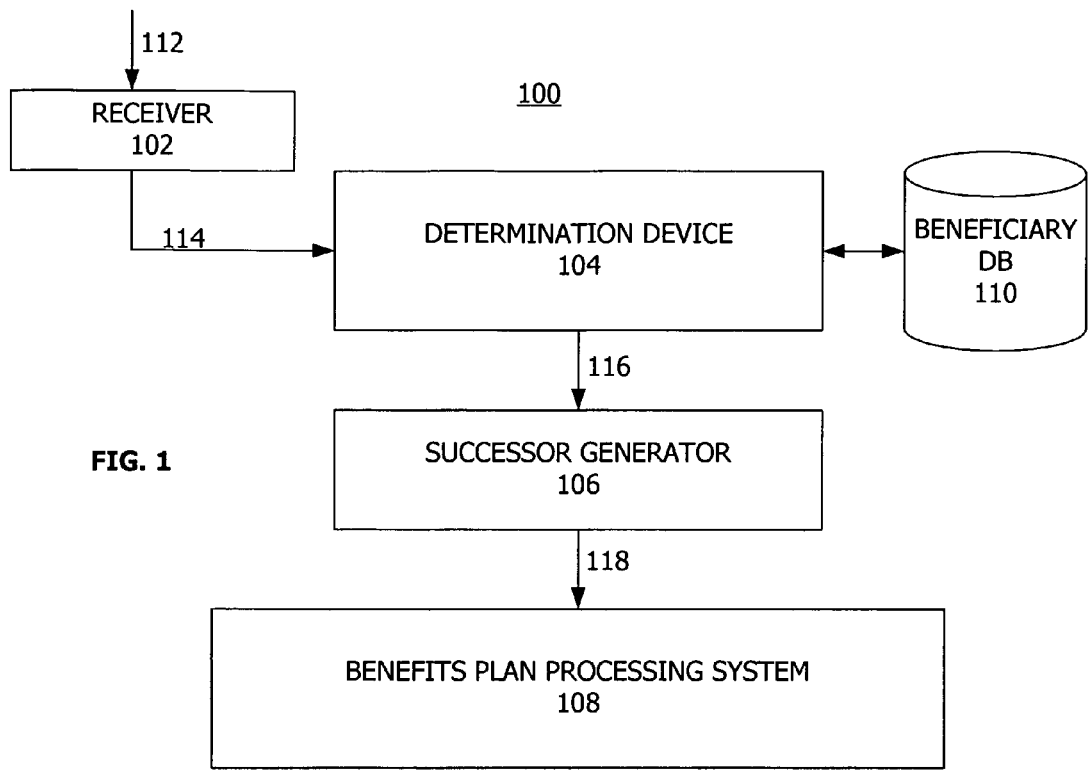
FIG. 1 illustrates an apparatus for electronic successor planning in a social benefits system.

FIG. 1 illustrates an apparatus 100 for electronic successor planning for a beneficiary. The apparatus 100 includes a receiver 102, a determination device 104, a successor generator 106, a benefit plans processing system 108 and a beneficiary database 110.

The apparatus 100 may be disposed in one or more processing environments, such as a stand alone or networked computing environment operating on a management software application or applications. The receiver 102 may be implemented in hardware, software or a combination thereof for receiving input commands, such as may be received from direct user input such as a keyboard or other data entry techniques, including for example electronic document submission or original content recognition on a scanned or facsimile document. The determination device 104 and the successor generator 106 may also be implemented in hardware, software or a combination thereof for performing executable processing operations as described in further detail below. The beneficiary database 110 may be any suitable storage device such as found within the processing environment of the apparatus 100 or may be stored in a location or device that can be subsequently accessed, such as for example a portable storage medium or an offsite accessible, possibly secured, data storage location. Additionally, the benefits plan processing system 108 may be any suitable software application executable on hardware for performing the administration aspects of a social benefits application running on the apparatus 100.

In one embodiment, the receiver 102 receives a benefits plan request 112. This request 112 may be received in one or more of a variety of techniques, including data entry by a social worker, data entry by the requesting person or entity, electronically across a processing interface, such as an Internet or other network based input, or any other suitable technique as recognized by one having ordinary skill in the art.

The receiver 102, upon receipt of the request 112 may extract extraneous information or other data to determine beneficiary data included therein. This beneficiary data 114 may then be provided to the determination device 104. The device 104 examines the beneficiary data and determines a current benefits plan. This determination may be in response to a specific plan request, such as included in request 112 or may also deduce or calculate the intended plan based on the information. For example, a user may enter a web-based request for a specific social benefits plan and this specific information is used to determine the plan. In another embodiment, a user may submit a standard benefits request that does not specifically indicate a particular plan, such that the device 104 determines which plan fits the request. It is also recognized that the determination device 104 may also verify the requested plan, if such information is included in the request 112 by determining if the beneficiary data 114 conforms to such request.

In one embodiment, the determination device 104 may access the beneficiary database 110 for retrieving or verifying entered information. For example, if a beneficiary has previously filled out an application, pertinent parts of the beneficiary data may be extracted from the database and the user does not need to re-enter this information, thus reducing data input requirements.

The determination device 104 thereby determines the current benefits plan 116. This benefits plan 116 is the plan that dictates at least a portion of the social benefits that the beneficiary is currently entitled to receive.

Although, in the apparatus 100, the generator 106 receives the current benefits plan 116, including the attendant beneficiary data. The generator 106 generates a successor benefits plan. This successor benefits plan may be any available social benefit plan that controls benefits to the beneficiary upon the completion of triggering events. As the current social plan is based on various factors, such as time, financial status, health of the user, among others, these factors are apt to change and as such the benefits plan also similarly adapts.

Once the successor plan 118 is generated, this plan is provided to the benefits plan processing system 108. The successor plan 118 may be generated by comparing the terms and/or conditions of the current benefits plan relative to logic succession plans. For example, some plans may include the addition of additional beneficiaries upon an event such as the birth of child or the plan may include changing the name of beneficiaries upon the death of a beneficiary. In the successor generator 106, there may be predetermined guidelines for which plans are possible successor plans for designated current plans.

It is also recognized that the current benefits plan is provided to the benefits plan processing system 108. In this system, the benefits plan operations may be performed. The current benefits plan may be actively managed in normal course. Furthermore, the benefits plan processing system 108 also maintains the successor benefits plan in the event any of the triggering events occurs. When such event occurs, the benefits plan processing system 108 may thereupon activate or enable the successor plan in proper succession to the termination of the current benefits plan.

Figure 2:
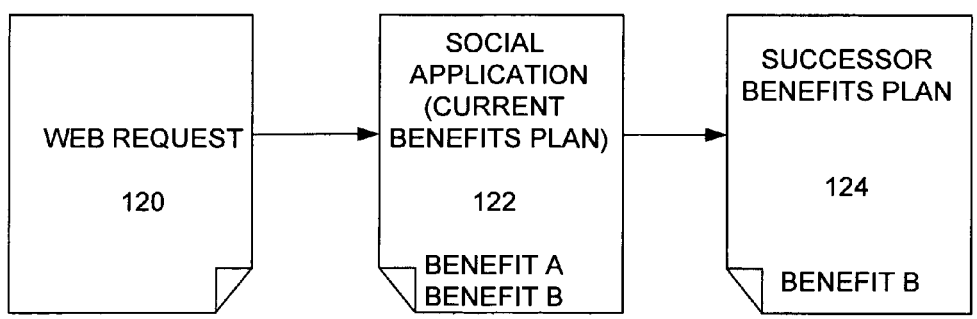
FIG. 2 illustrates a graphical illustration of a benefit succession plan in accordance with one embodiment of the present invention.

FIG. 2 illustrates a graphical representation of one embodiment of a social benefits plan solution. The illustration represents processing steps that may be performed by the apparatus 100 of FIG. 1. The solution includes a web request 120, where this request may be a portal-based request through a browser application or other type of recipient system, such as a mark-up language or proprietary networked browser application. The request 120 includes processing information, such as routing and other overhead information, as well as beneficiary data.

In the graphical solution of FIG. 2, a social application, also referred to as the current benefits plan, is generated from the web request. This benefit plan 122 includes the notation of benefits, such as sample benefits A and B. As discussed above, the current benefits plan indicates the current plan that the benefits processing system 108 manages.

Additionally, in this embodiment, the solution of FIG. 2 further includes the successor benefits plan 124. This plan 124 is generated based on the current benefits plan 122 and the plan includes the data that indicates benefits to be paid out in succession to the original benefits plan. Therefore, this benefits plan 124 may include data different from the beneficiary data in the web request 120, where in one embodiment this data may be acquired from the beneficiary database 110 of FIG. 1.

It is also recognized that this solution may include a scenario where the web request 120 improperly requests benefits to which the requester is not entitled. In the example of FIG. 2, the successor benefits plan 124 indicates that the beneficiary is only entitled to benefit B instead of both benefits A and B as originally requested. In this embodiment, a triggering event may be the ineligibility of the requestor for all of the requested benefits in the original request.

Figure 3:
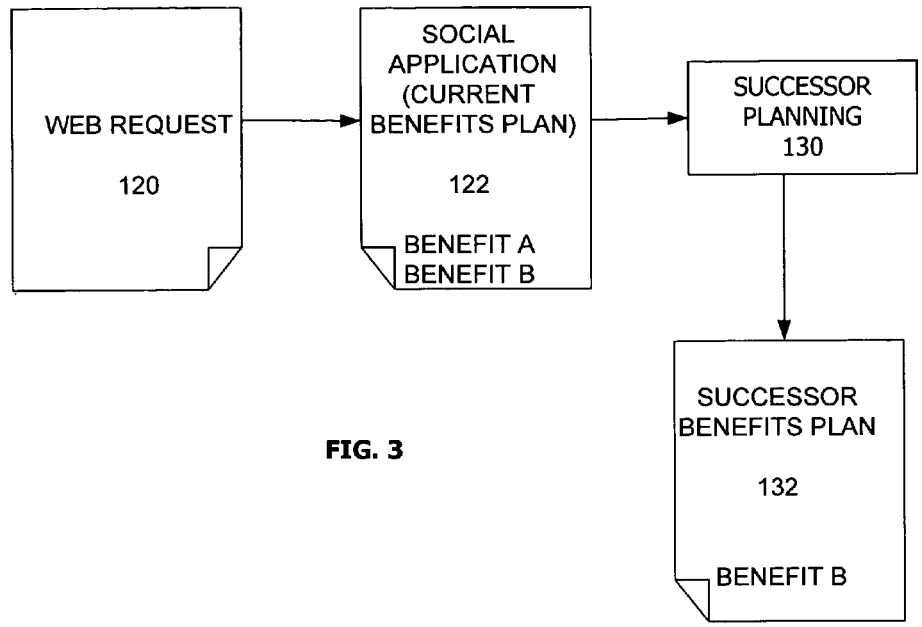
FIG. 3 illustrates a graphical illustration of a benefit succession plan in accordance with one embodiment of the present invention.

FIG. 3 illustrates another embodiment of a solution including the receipt of the web request 120 and the generation of the current benefits plan 122. In addition to the designation of benefits A and B for the requestor, the solution of FIG. 3 further includes a successor planning operation 130. This operation 130 may be similar to operations performed by generator 106 of FIG. 1.

In this embodiment, the successor planning operation 130 determines if a successor plan has been created. If no plan is created, the successor plan is therefore generated. This step may include the processing system creating a duplicate of the current benefits plan and thereupon generating the successor plan using the duplicated plan. As described above relative to FIG. 1, the successor plan may be generated based on possible successions of the existing plans as based on triggering events.

From the successor planning operation, the successor benefits plan 132 is generated. This plan 132 is illustrated as having a change in benefits to only benefit B, where based on a triggering event the beneficiary may have become ineligible for benefit A. With respect to FIG. 2, the plan 124 may be the same as the plan 132, but the plan 132 of FIG. 3 may be stored in the benefits plan processing system 108 whereas in the solution of FIG. 2, the current benefits plan 122 may not have been implemented because of the immediate occurrence of the triggering event, the beneficiary not being eligible for benefit A. In the solution of FIG. 3, the successor benefits plan 124 may not be activated for a longer period of time.

Figure 4:
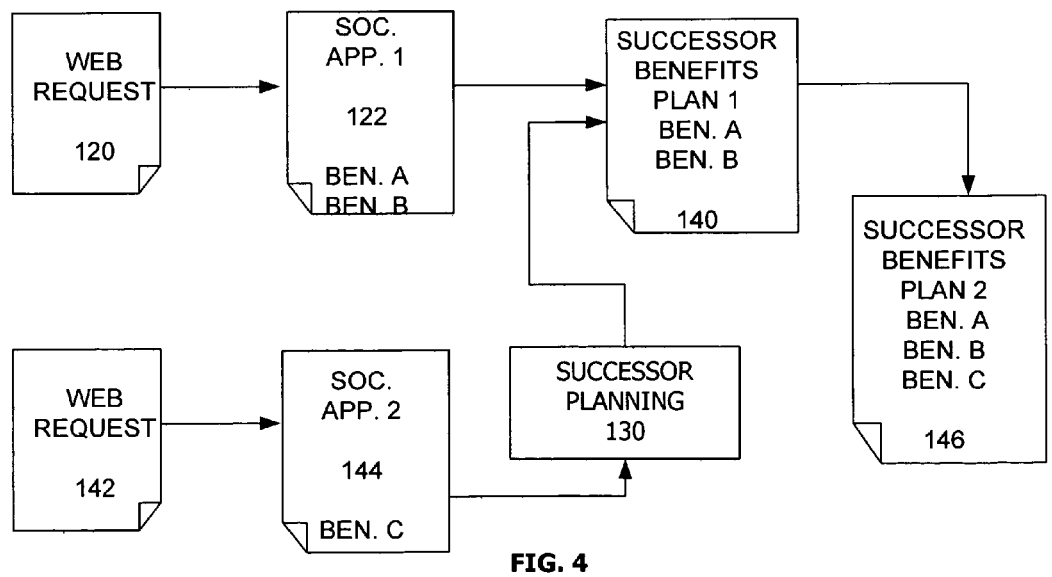
FIG. 4 illustrates a graphical representation of a benefit succession plan in accordance with one embodiment of the present invention.

FIG. 4 illustrates an embodiment of another solution for electronic successor benefits planning. This embodiment includes receipt of the web request 120, the generation of the current benefits plan 122 and the generation of a successor benefits plan 140 that includes benefits A and B to the beneficiary. Although, in the solution of FIG. 4, there is a change in the benefits plan because the beneficiary may request another benefit.

In this embodiment, a second web request 142 is received, which may be received similar to the web request 120. Similar to the processing operations for generating the benefits plan 122, the second current benefits plan 144 is also generated. As illustrated in FIG. 4, this plan includes the distribution of the benefit C to the beneficiary.

The second benefits plan 144 is also subjected to the successor planning operation 130. This successor planning operation assigns the right successor plan 140 to the second benefits application 144. In one embodiment, this electronic processing technique may include creating a new version of the succession benefits plan and executes the changes on the succession benefits plan based on the data in the second web request 142.

Based on the new request 142 and the successor planning 130, the successor benefits plan 140 is thereupon updated to generate the successor benefits plan 146. As illustrated in FIG. 4, the plan includes benefits A, B and C. In this solution, the triggering event may be the addition of a new request, specifically web request 142. Whereas previous benefit plan systems would require regeneration of the benefit plans for all three levels of benefits, the solution of FIG. 4 merely generates in a streamlined fashion the successor plan 146 combining the beneficiary's eligible benefits.

Figure 5:
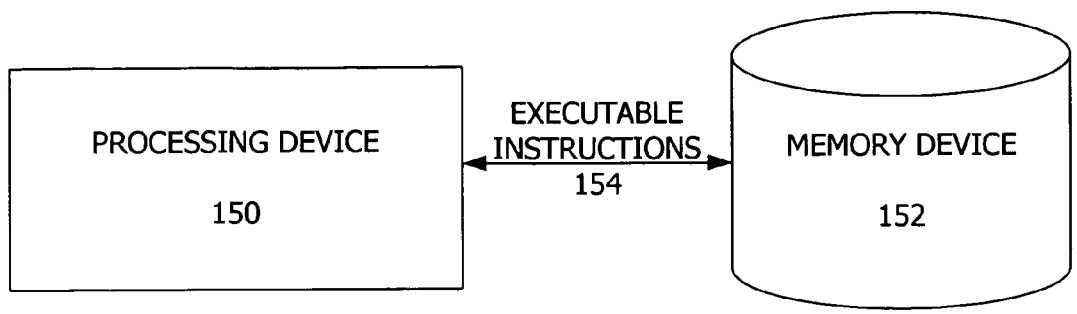
FIG. 5 illustrates one embodiment of an apparatus for electronic successor planning for a beneficiary.

FIG. 5 illustrates a processing device 150 and a memory device 152. The processing device 150 may be any suitable type of processing device including one or more processing components centrally disposed or in operative communication across one or more networked processing environments. The memory device 152 may be any suitable memory device having executable instructions 154 stored therein.

The processing device 150 is operative to perform processing operations in response to the executable instructions 154. These processing operations may be similar to the operations described above with respect to FIG. 1. Additionally, the operating device may be operative to perform the steps as describe with reference to FIG. 6 below.

Figure 6:
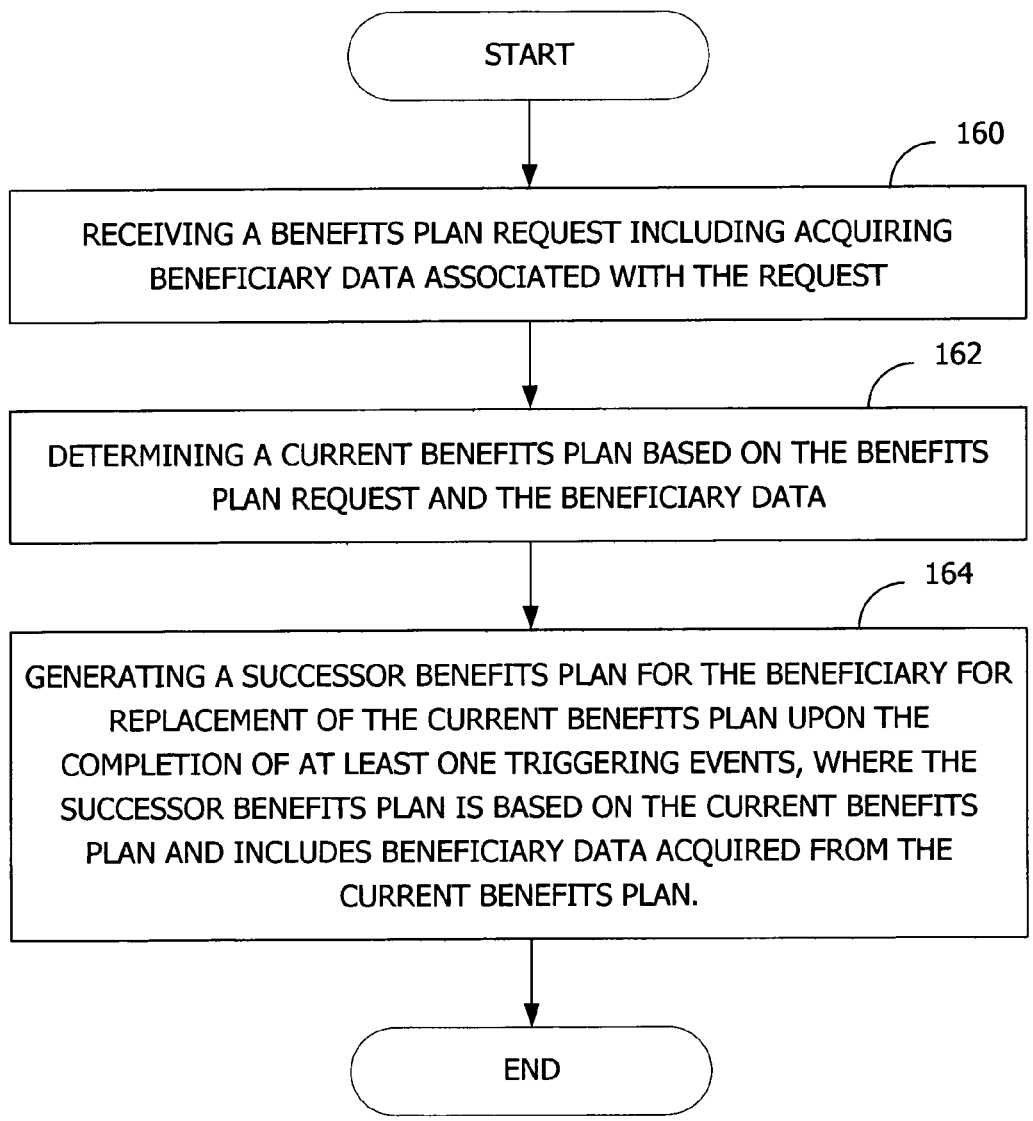
FIG. 6 illustrates a flowchart of the steps of one embodiment of a method for electronic successor planning for a beneficiary.

FIG. 6 illustrates a flowchart of the steps of one embodiment of a method for electronic successor planning for a beneficiary. In this embodiment, the method begins, step 160, by receiving a benefits plan request including acquiring beneficiary data associated with the request. This step may include receiving user-inputted information through, for example, a word processing application or a browser application. This step may include providing a user a template or other input form allowing for the receipt of specific information.

In one embodiment, this step may be performed by a beneficiary requesting a particular social benefit or may be entered by a social worker or other type of employee entering the information as received from the intended recipient. Additionally, this benefits plan request may be received across a network, such as an internet-based connection or an intranet connection, for example.

In this embodiment, the next step, step 162, is determining a current benefits plan based on benefits plan request and the beneficiary data. As described above, this step may be based on the type of form provided to a user in the web request, or in another embodiment may be determined based on the beneficiary information, such as determining for which benefits the recipient is eligible.

The next step, step 164, is generating a successor benefits plan for the beneficiary for the replacement of the current benefits plan upon the completion of at least one triggering event. In this step, the successor benefits plan may be based on the current benefits plan and includes beneficiary data acquired from the current benefits plan. Thereupon, the method is complete.

Although, in one embodiment, the step 164 may further include determining at least one change in social benefit processes and applying the change in the processes to the current benefits plan. For example, a change in processes may include how a benefit is provided or distributed to a particular beneficiary. In one embodiment of this step, a processing application performing the steps of this method may also create a duplicate version of the current benefits prior to applying the changes instead of recreating a whole new benefit plan.

In another embodiment of the method, similar to the solution illustrated in FIG. 4, the electronic successor planning may include detecting an existing benefits plan, comparing the beneficiary data of the existing benefits plan with the benefits plan request and then generating the successor benefits plans to account for the existing benefits plan. As illustrated in FIG. 4, the success benefits plan 146 accounts for the additional request 142 and plan 144.

Figure 7:
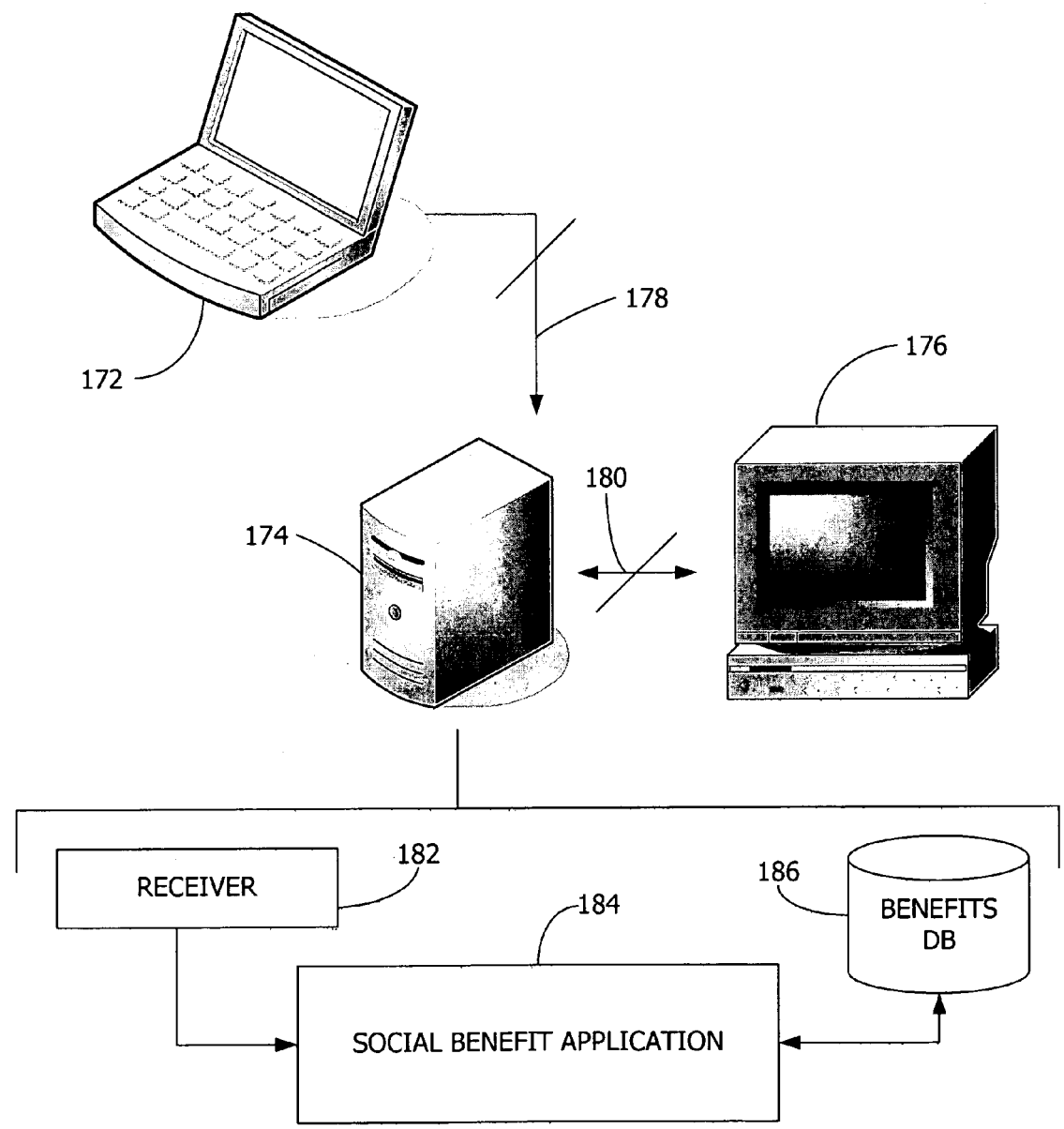
FIG. 7 illustrates a graphical representation of one embodiment of a system for electronic successor planning for a beneficiary.

FIG. 7 illustrates an exemplary embodiment of a system 170 for electronic successor planning. The system 170 includes a remote computer 172, a central processing system 174 and a remote terminal 176. The remote computer 172 and the remote terminal 176 may be coupled to the server 174 across networked connections 178 and 180. These connections 178, 180 may be, for example, intranet or internet connections allowing data communication therebetween.

The server 174 may be a central processing server including various processing components, which may implemented in hardware, software or a combination thereof. Among other elements, which have been omitted for clarity purposes only, the server includes a receiver 182, a social benefits application 184 and a benefits database 186. The receiver 182, may be similar to the receiver 102 of FIG. 1. The social benefits applications 184 includes various processing routines or programs that may be based on executable instructions provided to one or more processing devices within the server 174.

The social benefits application 184 is operative to perform the electronic successor benefit planning operations as described above, such as for example in the method of FIG. 6. It is through this application 184 that a user can enter beneficiary information through the remote computer 172. This information, received across the network 178 is processed and successor benefits plans determined. In sequential operations thereupon, one embodiment includes these benefits plans, current and successor plans, being accessible by the remote terminal 176. For example, a social worker may be able to access the plan information through the terminal 176. In another embodiment, a benefit processing system, such as an accounting or check processing system may access the server 174 across the network 180 from the remote terminal 176 to determine proper benefit payments.

It is through the electronic successor benefit planning that the processor of benefits may be streamlined. The automated process removes previous complications from multiple levels of user entry requirements. Furthermore, the automated process electronically simplifies the procedures when triggering events occur to not only limit benefit distribution disruptions, but also minimize user processing requirements, such as requiring a user to manually determine successor benefit plan and re-enter the plan information. As such, successor benefits plans improve current benefit plan process, such as the solution of FIG. 2 and provides proper succession procedures when a current benefit plan is generated.

Although the preceding text sets forth a detailed description of various embodiments, it should be understood that the legal scope of the invention is defined by the words of the claims set forth below. The detailed description is to be construed as exemplary only and does not describe every possible embodiment of the invention since describing every possible embodiment would be impractical, if not impossible. Numerous alternative embodiments could be implemented, using either current technology or technology developed after the filing date of this patent, which would still fall within the scope of the claims defining the invention.

It should be understood that there exist implementations of other variations and modifications of the invention and its various aspects, as may be readily apparent to those of ordinary skill in the art, and that the invention is not limited by specific embodiments described herein. It is therefore contemplated to cover any and all modifications, variations or equivalents that fall within the scope of the basic underlying principals disclosed and claimed herein.

What is claimed is:

1. A method for electronic successor planning for a beneficiary, the method comprising:
   receiving, by a computer processor, a benefits plan request including acquiring beneficiary data associated with the benefits plan request;
   searching, by the computer processor, a beneficiary database to verify the acquired beneficiary data;
   identifying, by the computer processor, an existing benefits plan from the beneficiary database based on the benefits plan request and the acquired beneficiary data;
   comparing, by the computer processor, the identified existing benefits plan with the benefits plan request;
   determining, by the computer processor, changes needed to be made to the identified existing benefits plan;
   creating, by the computer processor, a duplicate version of the identified existing benefits plan prior to applying the changes;
   applying, by the computer processor, the changes to generate a first current benefits plan for the benefits plan request;
   upon receiving a second benefits plan request for an additional benefit, generating, by the computer processor, a second current benefits plan by repeating steps that generated the current benefits plan;
   receiving a benefits plan request from a beneficiary identified in the existing benefits plan; and
   generating, by the computer processor, a successor benefits plan for the beneficiary for replacement of the first and second current benefits plans upon completion of at least one triggering event, where the successor benefits plan is based on both the first and second current benefits plans, the beneficiary's requested benefits, and combines benefits provided by the first and second current benefits plans, and the beneficiary's requested benefits.

2. The method of claim 1 further comprising:
   receiving the benefits plan request from a networked request.

3. The method of claim 1 wherein the first or second current benefits plan indicates at least one social benefit for the beneficiary and the successor benefits plan indicates at least one anticipated social benefit for the beneficiary, wherein the anticipated social benefit for the successor benefits plan includes at least one of the social benefits of the first or second current benefits plan.

4. The method of claim 1 wherein generating a successor benefits plan includes:
   determining, by the computer processor, at least one change in social benefits processes; and
   applying, by the computer processor, the change in processes to the first or second current benefit plan.

5. The method of claim 4 further comprising:
   creating, by the computer processor, a duplicate version of the first or second current benefits plan prior to applying the changes.

6. The method of claim 1, wherein each of the first and second benefits plan requests is a request for a specific social benefits plan or a standard benefits request.

7. The method of claim 6, further comprising, in response to either the first or the second benefits plan request being a standard benefits request, determining a plan that meets requirement of the standard benefits request.

8. An apparatus for electronic successor planning for a beneficiary comprising:
   a memory device having executable instructions stored therein; and
   a processing device coupled to the memory device and receiving the executable instructions therefrom, the processing device, in response to the executable instructions, operative to:
   receive a benefits plan request including acquiring beneficiary data associated with the benefits plan request;
   searching a beneficiary database to verify the acquired beneficiary data;
   identify an existing benefits plan from the beneficiary database based on the benefits plan request and the acquired beneficiary data;
   compare the identified existing benefits plan with the benefits plan request;
   determine changes need to be made to the identified existing benefits plan;
   create a duplicate version of the identified existing benefits plan prior to applying the changes;
   apply the changes to generate a first current benefits plan for the benefits plan request;
   upon receiving a second benefits plan request for an additional benefit, generate a second current benefits plan by repeating steps that generated the current benefits plan;
   receive a benefits plan request from a beneficiary identified in the existing benefits plan; and
   generate a successor benefits plan for the beneficiary for replacement of the first and second current benefits plans upon completion of at least one triggering event, where the successor benefits plan is based on both the first and second current benefits plans, the beneficiary's plan, and combines benefits provided by the first and second current benefits plans, and the beneficiary's requested benefits.

9. The apparatus of claim 8, the processing device further operative to:
receive the benefits plan request from a networked request.

10. The apparatus of claim 8 wherein the first or second current benefits plan indicates at least one social benefit for the beneficiary and the successor benefits plan indicates at least one anticipated social benefit for the beneficiary, wherein the anticipated social benefit for the successor benefits plan includes at least one of the social benefits of the first or second current benefits plan.

11. The apparatus of claim 8, wherein the processing device when performing generating a successor benefits plan further:
determines at least one change in social benefits processes; and
applies the change in processes to the first or second current benefit plan.

12. The apparatus of claim 11, the processing device further operative to:
create a duplicate version of the first or second current benefits plan prior to applying the changes.

13. The apparatus of claim 8, wherein each of the first and second benefits plan requests is a request for a specific social benefits plan or a standard benefits request.

14. The apparatus of claim 13, the processing device further operative to: in response to either the first or the second benefits plan request being a standard benefits request, determine a plan that meets requirement of the standard benefits request.

* * * * *